(12) United States Patent
Southwell et al.

(10) Patent No.: US 11,291,501 B2
(45) Date of Patent: Apr. 5, 2022

(54) RADIO FREQUENCY ABLATION SYSTEMS

(71) Applicant: Medical Engineering Innovations, Inc., Madison, WI (US)

(72) Inventors: Steven Charles Southwell, Madison, WI (US); Joshua Cook, Madison, WI (US); Tim Holzmann, Madison, WI (US); David Strait, Madison, WI (US); Richard Schmidt, Madison, WI (US)

(73) Assignee: Medical Engineering Innovations, Inc., Madison, WI (US)

( * ) Notice: Subject to any disclaimer, the term of this patent is extended or adjusted under 35 U.S.C. 154(b) by 0 days.

(21) Appl. No.: 16/405,190

(22) Filed: May 7, 2019

(65) Prior Publication Data

US 2020/0268444 A1 Aug. 27, 2020

Related U.S. Application Data

(60) Provisional application No. 62/811,224, filed on Feb. 27, 2019.

(51) Int. Cl.
*A61B 18/18* (2006.01)
*A61B 18/12* (2006.01)
(Continued)

(52) U.S. Cl.
CPC ............ *A61B 18/18* (2013.01); *A61B 5/4244* (2013.01); *A61B 18/1206* (2013.01); *A61B 18/14* (2013.01);
(Continued)

(58) Field of Classification Search
CPC .......... A61B 2018/00529; A61B 2018/00577; A61B 2018/1405; A61B 2018/1412; A61B 2018/1415; A61B 2018/143; A61B 18/14
See application file for complete search history.

(56) References Cited

U.S. PATENT DOCUMENTS 5,217,460 A * 6/1993 Knoepfler ............... A61B 17/29
606/1
8,235,991 B2 * 8/2012 Mauti ................ A61B 18/1477
606/34

(Continued)

OTHER PUBLICATIONS

Wolf DC. Evaluation of the Size, Shape, and Consistency of the Liver. In: Walker HK, Hall WD, Hurst JW, editors. Clinical Methods: The History, Physical, and Laboratory Examinations. 3rd edition. Boston: Butterworths; 1990. Ch. 94 (pp. 478-481). See: https://www.ncbi.nlm.nih.gov/books/NBK421/ (Year: 1990).*

(Continued)

*Primary Examiner* — Ronald Hupczey, Jr.
*Assistant Examiner* — Bradford C. Blaise
(74) *Attorney, Agent, or Firm* — Casimir Jones S.C.; J. Mitchell Jones (57) ABSTRACT

The present invention relates to systems for use for radio frequency ablation. The systems can include one or more of an ablation tool, power source for use with the ablation tool and a backstop for use in conjunction with the ablation tool during surgical procedures. Preferred ablation tools comprise a series of three or more blade-shaped electrodes disposed in a linear, curved, curvilinear or circular array. The backstops are useful for reducing direct physical and thermal heat transfer injuries to the patient or surgeon during procedures using radiofrequency (RF) ablation devices.

19 Claims, 9 Drawing Sheets

(51) Int. Cl.
  *A61B 5/00* (2006.01)
  *A61B 18/00* (2006.01)
  *A61B 18/14* (2006.01)
(52) U.S. Cl.
  CPC .............. *A61B 2018/00529* (2013.01); *A61B 2018/00577* (2013.01); *A61B 2018/143* (2013.01); *A61B 2018/1405* (2013.01); *A61B 2018/1412* (2013.01); *A61B 2018/1415* (2013.01)

(56) References Cited

U.S. PATENT DOCUMENTS

| | | | |
|---|---|---|---|
| 2004/0162551 A1* | 8/2004 | Brown | A61B 18/1477 606/41 |
| 2004/0181216 A1* | 9/2004 | Kelly | A61B 18/1477 606/41 |
| 2005/0171534 A1 | 8/2005 | Habib | |
| 2006/0064084 A1 | 3/2006 | Haemmerich et al. | |
| 2006/0241588 A1 | 10/2006 | Heim et al. | |
| 2007/0125662 A1* | 6/2007 | Dumont | A61B 18/1477 205/701 |
| 2009/0036882 A1* | 2/2009 | Webster | A61B 18/1477 606/33 |
| 2009/0076497 A1 | 3/2009 | Morris et al. | |
| 2009/0306652 A1* | 12/2009 | Buysse | A61B 90/11 606/41 |
| 2012/0130269 A1* | 5/2012 | Rea | A61B 5/0488 600/554 |
| 2013/0144284 A1* | 6/2013 | Behnke, II | A61B 18/1815 606/33 |

OTHER PUBLICATIONS

International Search Report & Written Opinion, Int'l Patent Application No. PCT/US2020/020138, dated Jun. 24, 2020, 15 pages.

* cited by examiner

RADIO FREQUENCY ABLATION SYSTEMS

CROSS REFERENCE TO RELATED APPLICATIONS

This application claims the benefit of U.S. Prov. Appl. 62/811,224 filed on Feb. 27, 2019, the entire contents of which are incorporated herein by reference.

FIELD OF THE INVENTION

The present invention relates to systems for use for radio frequency ablation.

BACKGROUND OF THE INVENTION

Liver resection is still the management of choice with the best chance for long-term cure in patients with primary and metastatic hepatic tumors. However, only a small percentage of these patients are candidates for curative surgical resection, because of the tumor size, location near major intrahepatic vessels, multifocality, or inadequate hepatic function related to coexistent cirrhosis. Traditionally, for a tumor to be considered appropriate for curative resection, there must not be any extrahepatic disease or severe hepatic dysfunction, the tumor or tumors must not be so extensive that too little functioning liver remains after the resection, and at least a 1-cm tumor-free resection margin should be attained and there should not be any involvement of the confluence of the portal vein.

Radio frequency (RF) ablation has become a widely used ablative technique for primary and secondary liver tumors and its safety, efficacy, and acceptable local recurrence and short-term survival rates had been well demonstrated in the literature. RF ablation is a technique based on the conversion of electromagnetic energy into heat to destroy tumors in various organs. It is either a useful adjunct therapy to partial liver resection or the primary modality of treatment for patients who were not candidates for curative resection.

Devices for use in RF ablation have been described. See, e.g., U.S. Pat. Nos. 7,367,974 and 10,130,415, both of which are incorporated herein by reference in their entirety. Some of the devices utilize an array of electrodes which are inserted into a target organ such as a liver. The tissue adjacent to the electrodes is coagulated, allowing resection of a portion of the organ. The devices described in U.S. Pat. Nos. 7,367,974 and 10,130,415 utilize electrodes which are slidable in the handpiece. Devices such as the Habib 4X are currently in the marketplace. The Habib 4X utilizes four needle-shaped electrodes in a square array. Procedures with this device require multiple insertions and long periods of energy delivery. Additionally, the small diameter needle-like electrodes become very hot, which can result in tissue sticking to the electrodes.

Problems with RF devices with slidable electrodes include difficulty of use and manufacture. Another problem with RF ablation devices in general is that energy from the device may cause unintended heating in adjacent tissues or even of a surgeon's hand. Compared with these existing devices, the devices of the present invention have improved usability and can ablate circular, linear, curved or curvilinear regions of a target tissue in an efficient manner.

SUMMARY OF THE INVENTION

The present invention relates to systems for use for radio frequency ablation. The systems can include one or more components including an ablation tool (i.e., an ablation handpiece or just handpiece), power source for use with the ablation tool and a backstop for use in conjunction with the ablation tool during surgical procedures. Preferred ablation tools comprise a series of three or more blade-shaped electrodes disposed in a linear, curved, curvilinear or circular array. The backstops are useful for reducing direct physical and thermal heat transfer injuries to the patient or surgeon during procedures using radiofrequency (RF) ablation devices.

In some preferred embodiments, the present invention provides an ablation apparatus comprising: a radio frequency (RF) power source; a series of three or more blade-shaped electrodes that are electrically connected to the RF power source, the blade-shaped electrodes each having a tissue-piercing distal end; and an electrically insulated holder, the three or more blade shaped electrodes non-slidably positioned (i.e., are in fixed positions) in the electrically insulated holder wherein the blade-shaped electrodes are oriented so that when alternating current power is applied via the RF power source to a pair of blade-shaped electrodes a current flows between the adjacent blade-shaped electrodes.

In some preferred embodiments, RF power source applies the alternating current to a pair or pairs of adjacent blade-shaped electrodes. In some preferred embodiments, the RF power source applies the alternating current to a pair or pairs of non-adjacent blade-shaped electrodes. In some preferred embodiments, the apparatus comprises from between 3 and 20 blade-shaped electrodes. In some preferred embodiments, the apparatus comprises from 3 to 10 blade-shaped electrodes. In some preferred embodiments, the blade-shaped electrodes are positioned in the holder in a linear array. In some preferred embodiments, the blade-shaped electrodes are positioned in the holder in a circular, oval or elliptical array. In some preferred embodiments, the blade-shaped electrodes are positioned in the holder in a curved array. In some preferred embodiments, the blade-shaped electrodes are positioned in the holder in a curvilinear array. In some preferred embodiments, the blade-shaped electrodes are positioned in the holder to form an open array. In some preferred embodiments, the blade-shaped electrodes are positioned in the holder to form a closed array.

In some preferred embodiments, the blade-shaped electrodes comprise two opposing planar surfaces defining a width and planar axis and two opposing edges defining a thickness and the blade shaped electrodes are characterized in having a greater width than thickness. In some embodiments, the blade-shaped electrodes have a rectangular cross section, while in other embodiments, the blade-shaped electrodes may have a diamond-shaped cross section, parallelogram-shaped cross section and/or comprise ribs, ridges or similar features. In general, the width to thickness ratio is greater than 3:1 and can be up to about 10:1 or 20:1. In some preferred embodiments, the blade-shaped electrodes are positioned in the holder so that the planar axes of the blade-shaped electrodes are substantially parallel to a radial line of a curved holder. In some preferred embodiments, the blade-shaped electrodes are positioned in the holder so that the planar axes of the blade-shaped electrodes are substantially perpendicular to a radial line of a curved holder. In some preferred embodiments, the blade-shaped electrodes are positioned in the holder so that the planar axes of the blade-shaped electrodes are substantially perpendicular to a long axis of a linear holder. In some preferred embodiments, the blade-shaped electrodes are uniformly spaced in the holder. In some preferred embodiments, the blade-shaped electrodes contain depth markings.

In some preferred embodiments, the RF power source comprises a single-channel RF generator with switching to provide energy independently to pairs or groups of the blade-shaped electrodes. In some preferred embodiments, the RF power source comprises a multi-channel RF generator with dedicated RF amplifiers for selected pairs or groups of the blade-shaped electrodes. In some preferred embodiments, the RF power source comprises control circuits to control average current flow at the electrodes according to at least one parameter selected from the group consisting of: local temperature of the tissue, local impedance of the tissue, a predetermined current limit, and a predetermined power limit.

In some preferred embodiments, the present invention provides methods of tissue ablation comprising: providing an ablation apparatus as described above; inserting the blade-shaped electrodes into a tissue to be ablated; applying alternating current via said RF power source so that a current flows between designated pairs or groups of electrodes thereby creating a zone of ablated tissue. In some preferred embodiments, the tissue is an organ and the zone of ablated tissue forms a partition across the organ and further comprising cutting the tissue of the organ at the partition of ablated tissue to reduce blood loss during resection of the organ. In some preferred embodiments, the partition of ablated tissue is positioned between the portion of the organ to be resected and a region of blood flow into the tissue. In some preferred embodiments, the organ is a liver.

In some preferred embodiments, the present invention provides ablation apparatus as described above for use in ablating a tissue or resecting an organ. In some preferred embodiments, the tissue is an organ. In some preferred embodiments, the organ is a liver. In some preferred embodiments, the tissue is tumor tissue. In some preferred embodiments, the tissue is uterine tissue.

In some preferred embodiments, the present invention provides an article for use in conjunction with an ablation tool comprising two or more electrode units having tissue piercing distal portions, comprising: a backstop formed from an electrically nonconductive material, the backstop having an upper surface and a lower surface; and a plurality of tissue support structures extending upward from the backstop, the tissue support structures spaced to support a target organ above the backstop when the article is placed underneath the organ and to receive the tissue piercing distal portions of the two or more electrode units so that the electrode units pass through and extend beyond the organ and the tissue piercing distal portions contact the backstop.

In some preferred embodiments, the backstop has a shape selected from the group consisting of a planar shape, and rounded shape, a curved shape, a partial cylindrical shape and a partial spherical shape. In some preferred embodiments, the tissue support structures have a shape selected from the group consisting of pillars, ridges, rounded-cones, triangular cones, truncated cones, cylinders, and combinations thereof. In some preferred embodiments, the pillars have a cross-section shape selected from the group consisting of circular, oval, elliptical, square and triangular cross-sections. In some preferred embodiments, the backstop further contains a conductive layer. In some preferred embodiments, the conductive layer is attached to a ground. In some preferred embodiments, the backstop has a hollow cavity therein to provide thermal insulation. In some preferred embodiments, the backstop has a rim extending around the perimeter of the backstop to provide a basin for receiving fluid expressed from the organ during ablation.

In some preferred embodiments, the lower surface of the backstop comprises a plurality of hand support structures extending therefrom to reduce heat transfer from the backstop to the hand of a user. In some preferred embodiments, the hand support structures are selected from the group consisting of pillars, ridges, rounded-cones, triangular cones, truncated cones, cylinders, and combinations thereof. In some preferred embodiments, the pillars have a cross-section shape selected from the group consisting of circular, oval, elliptical, square and triangular cross-sections.

In some preferred embodiments, the present invention provides systems for use in resection of a target organ comprising: a radio frequency (RF) ablation tool comprising one or more electrode units positioned in a holder having tissue piercing distal portions; and a backstop formed from an electrically non-conductive material, the backstop having an upper surface and a lower surface and a plurality of tissue support structures extending upward from the upper surface of the backstop, the tissue support structures spaced to support a target organ above the backstop when the article is placed underneath the organ and to receive the tissue piercing distal portions of the two or more electrode units so that the electrode units pass through and extend beyond the organ and the tissue piercing distal portions contact the backstop.

In some preferred embodiments, the backstop has a shape selected from the group consisting of a planar shape, and rounded shape, a curved shape, a partial cylindrical shape and a partial spherical shape. In some preferred embodiments, the tissue support structures have a shape selected from the group consisting of pillars, ridges, rounded-cones, triangular cones, truncated cones, cylinders, and combinations thereof. In some preferred embodiments, the pillars have a cross-section shape selected from the group consisting of circular, oval, elliptical, square and triangular cross-sections. In some preferred embodiments, the backstop further contains a conductive layer. In some preferred embodiments, the conductive layer is attached to a ground. In some preferred embodiments, the backstop has a hollow cavity therein to provide thermal insulation. In some preferred embodiments, the backstop has a rim extending around the perimeter of the backstop to provide a basin for receiving fluid expressed from the organ during ablation.

In some preferred embodiments, the lower surface of the backstop comprises a plurality of hand support structures extending therefrom to reduce heat transfer from the backstop to the hand of a user. In some preferred embodiments, the hand support structures are selected from the group consisting of pillars, ridges, rounded-cones, triangular cones, truncated cones, cylinders, and combinations thereof. In some preferred embodiments, the pillars have a cross-section shape selected from the group consisting of circular, oval, elliptical, square and triangular cross-sections.

In some preferred embodiments, the RF ablation tool is electrically connected to an RF power source. In some preferred embodiments, the RF ablation tool comprises two or more electrode units and the electrode units are oriented so that when alternating current is applied to either the first or second electrode unit, a current flows from that electrode unit to the other electrode unit. In some preferred embodiments, the electrode unit is a blade-shaped electrode. In some preferred embodiments, the blade-shaped electrodes are non-slidably positioned (i.e., provided in a fixed position) in the holder. In some preferred embodiments, the apparatus comprises from between 3 and 20 blade-shaped electrodes. In some preferred embodiments, the apparatus comprises from 3 to 10 blade-shaped electrodes. In some preferred embodiments, the blade-shaped electrodes are positioned in the holder in a linear array. In some preferred embodiments, the blade-shaped electrodes are positioned in the holder in a circular, oval or elliptical array. In some preferred embodiments, the blade-shaped electrodes are positioned in the holder in a curved array. In some preferred embodiments, the blade-shaped electrodes are positioned in the holder in a linear array. In some preferred embodiments, the blade-shaped electrodes are positioned in the holder in a curvilinear array. In some preferred embodiments, the blade-shaped electrodes are positioned in the holder to form an open array. In some preferred embodiments, the blade-shaped electrodes are positioned in the holder to form a closed array.

In some preferred embodiments, the blade-shaped electrodes comprise two opposing planar surfaces defining a width and planar axis and two opposing edges defining a thickness and the blade shaped electrodes are characterized in having a greater width than thickness. In some embodiments, the blade-shaped electrodes have a rectangular cross section, while in other embodiments, the blade-shaped electrodes may have a diamond-shaped cross section, parallelogram-shaped cross section and/or comprise ribs, ridges or similar features. In general, the width to thickness ratio is greater than 3:1 and can be up to about 10:1 or 20:1. In some preferred embodiments, the blade-shaped electrodes are positioned in the holder so that the planar axes of the blade-shaped electrodes are substantially parallel to a radial line of a curved array. In some preferred embodiments, the blade-shaped electrodes are positioned in the holder so that the planar axes of the blade-shaped electrodes are substantially perpendicular. In some preferred embodiments, the blade-shaped electrodes are positioned in the holder so that the planar axes of the blade-shaped electrodes are substantially perpendicular to a long axis of a linear holder. In some preferred embodiments, the blade-shaped electrodes are uniformly spaced in the holder. In some preferred embodiments, the blade-shaped electrodes contain depth markings.

In some preferred embodiments, the RF power source comprises a single-channel RF generator with switching to provide energy independently to pairs or groups of the blade-shaped electrodes. In some preferred embodiments, the RF power source comprises a multi-channel RF generator with dedicated RF amplifiers for selected pairs or groups of the blade-shaped electrodes. In some preferred embodiments, each electrode unit comprises an array of two or more needle shaped electrodes. In some preferred embodiments, the electrode units are collapsible. In some preferred embodiments, the ablation tool comprises from 2 to 10 electrode units with needle-shaped electrodes of collapsible electrode units. In some preferred embodiments, the RF power source comprises control circuits to control average current flow at the electrodes according to at least one parameter selected from the group consisting of: local temperature of the tissue, local impedance of the tissue, a predetermined current limit, and a predetermined power limit.

In still further preferred embodiments, the present invention provides systems for use in resection of a target organ comprising: a radio frequency (RF) power source; a series of three or more blade-shaped electrodes that are electrically connected to the RF power source, the blade-shaped electrodes each having a tissue-piercing distal end; an electrically insulated holder, the three or more blade shaped electrodes non-slidably positioned in the electrically insulated holder, wherein the blade-shaped electrodes are oriented so that when alternating current power is applied via the RF power source to a pair of blade-shaped electrodes a current flows between the adjacent blade-shaped electrodes; and a backstop formed from an electrically non-conductive material, the backstop having an upper surface and a lower surface and a plurality of tissue support structures extending upward from the upper surface of the backstop, the tissue support structures spaced to support a target organ above the backstop when the backstop is placed underneath the organ and to receive the tissue piercing distal ends of the three or more blade-shaped electrodes positioned in the electrically insulated holder so that the electrodes pass through and extend beyond the organ and the tissue piercing distal portions contact the backstop.

In some preferred embodiments, the from 3 to 10 blade-shaped electrodes are non-slidably positioned in the electrically insulated holder. In some preferred embodiments, the blade-shaped electrodes are positioned in the holder in an array selected from the group consisting of a linear array, a curved array, a curvilinear array, a circular array, an oval array and an elliptical array. In some preferred embodiments, the blade-shaped electrodes comprise two opposing planar surfaces defining a width and a planar axis and two opposing edges defining a thickness and the blade shaped electrodes are characterized in having a greater width than thickness. In some preferred embodiments, the blade-shaped electrodes are positioned in the holder so that the planar axes of the blade-shaped electrodes are substantially parallel to a radial line of a curved electrically insulated holder. In some preferred embodiments, the blade-shaped electrodes are positioned in the holder so that the planar axes of the blade-shaped electrodes are substantially perpendicular to a radial line of a curved electrically insulated holder. In some preferred embodiments, the blade-shaped electrodes are positioned in the holder so that the planar axes of the blade-shaped electrodes are substantially perpendicular to a long axis of a linear electrically insulated holder. In some preferred embodiments, the blade-shaped electrodes are uniformly spaced in the electrically insulated holder. In some preferred embodiments, the RF power source comprises a multi-channel RF generator with dedicated RF amplifiers for selected pairs or groups of the blade-shaped electrodes. In some preferred embodiments, the RF power source applies the alternating current to a pair or pairs of adjacent blade-shaped electrodes. In some preferred embodiments, the RF power source applies the alternating current to a pair or pairs of non-adjacent blade-shaped electrodes.

In some preferred embodiments, the backstop has a shape selected from the group consisting of a planar shape, and rounded shape, a curved shape, a partial cylindrical shape and a partial spherical shape. In some preferred embodiments, the tissue support structures have a shape selected from the group consisting of pillars, ridges, rounded-cones, triangular cones, truncated cones, cylinders, and combinations thereof. In some preferred embodiments, the backstop further contains a conductive layer between the upper and lower surfaces. In some preferred embodiments, the conductive layer is attached to a ground. In some preferred embodiments, the backstop has a thermal break positioned between the upper and lower surfaces. In some preferred embodiments, the thermal break is provided by a hollow cavity positioned between the upper and lower surfaces. In some preferred embodiments, the backstop further has a rim extending around the perimeter of the backstop to provide a basin for receiving fluid expressed from the organ during ablation. In some preferred embodiments, the lower surface of the backstop comprises a plurality of hand support structures extending therefrom to reduce heat transfer from the backstop to the hand of a user. In some preferred embodiments, the hand support structures are selected from the group consisting of pillars, ridges, rounded-cones, triangular cones, truncated cones, cylinders, and combinations thereof.

In some preferred embodiments, the present invention provides methods of ablating a target tissue comprising: contacting the target tissue with a backstop as described above so that the organ is supported on the plurality of upwardly extending tissue support structures, inserting one or more electrode units of an RF ablation tool into the tissue to define a resection line or area to be ablated, wherein the electrode units have tissue piercing distal portions, so that the electrode units extend through the tissue and the tissue piercing distal portions exit the organ to contact the upper surface of the backstop; and applying RF power to the electrodes to coagulate tissue along the resection line or in the area to be ablated. In some preferred embodiments, the tissue is an organ. In some preferred embodiments, the tissue is tumor tissue. In some preferred embodiments, the organ is a liver or uterus. In some preferred embodiments, the tissue is an organ and the methods further comprise resecting the organ along the resection line. In some preferred embodiments, ablation of tissue within the organ creates a partition positioned between the portion of the organ to be resected and a region of blood flow into the tissue.

In some preferred embodiments, the present invention provides a backstop as described above for use to support a tissue for ablation or an organ for resection by an RF ablation tool. In some preferred embodiments, the organ is a liver or uterus.

In some preferred embodiments, the present invention provides an ablation system as described above for use in ablating a tissue or resecting an organ. In some preferred embodiments, the organ is a liver or uterus. In some preferred embodiments, the tissue is tumor tissue.

DETAILED DESCRIPTION OF THE INVENTION

The present invention relates to systems for use for radio frequency ablation. In preferred embodiments, the present invention provides systems that include one or more of an ablation tool, power source for use with the ablation tool and a backstop device for use in conjunction with the ablation tool during surgical procedures. In some preferred embodiments, the ablation tool comprises a series of three or more electrodes disposed in a linear, curved, curvilinear, or circular arrangements or arrays. In some particularly preferred embodiments, the electrodes are blade-shaped. In still further preferred embodiments, it is contemplated that the backstop devices are useful for reducing direct physical and thermal heat transfer injuries to the patient or surgeon during procedures using radiofrequency (RF) ablation tools.

RF ablation tools are known in the art. See, e.g., U.S. Pat. No. 7,367,974 (incorporated herein by reference in its entirety). RF ablation tools can generally comprise a plurality of electrodes and are connected to a RF source so that electric fields may be generated between the electrodes. The ablation tools and systems provided herein address problems with these previous devices by enhancing usability (e.g., by a surgeon) and efficiency during ablation procedures.

Figure 1A:
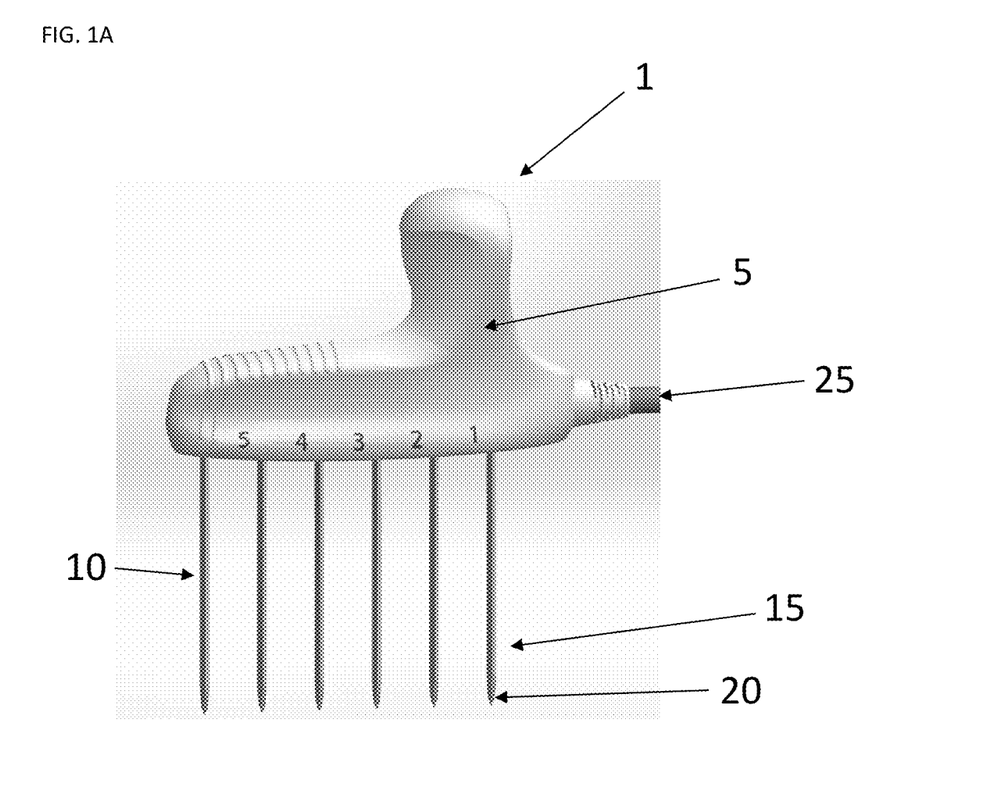
FIG. 1A is perspective view of an RF ablation tool of the present invention.

Referring to FIG. 1A, an RF ablation tool 1 is depicted. The RF ablation tool 1 comprises a holder 5 supporting a plurality of elongate electrodes 10. The elongate electrodes each have a tissue piercing distal portion 15 such as a sharpened tip 20. In some embodiments, the electrode is blade-shaped. The holder 5 may be, for example, an insulating material block having holes cut in the holder 5 to receive metallic shafts of the elongate electrodes 10 at regular intervals. In a preferred embodiment, the separation of the electrodes 10 is from 0.5 to 2.0 cm. The elongate electrodes 10 may be fixed to the holder 10 so as to be moved in unison for rapid insertion. In other words, the electrodes are fixed in the holder so that they do not slide within the holder. It has been found that even when blade-shaped electrodes are utilized, the electrodes may be inserted into a target organ such as a liver in unison so that an ablation or resection line is defined within (or across) the target organ. This allows ablation of a defined area with the target organ in a time-efficient manner which addresses problems associated with devices which utilize sliding electrodes or small arrays.

Figure 1B:
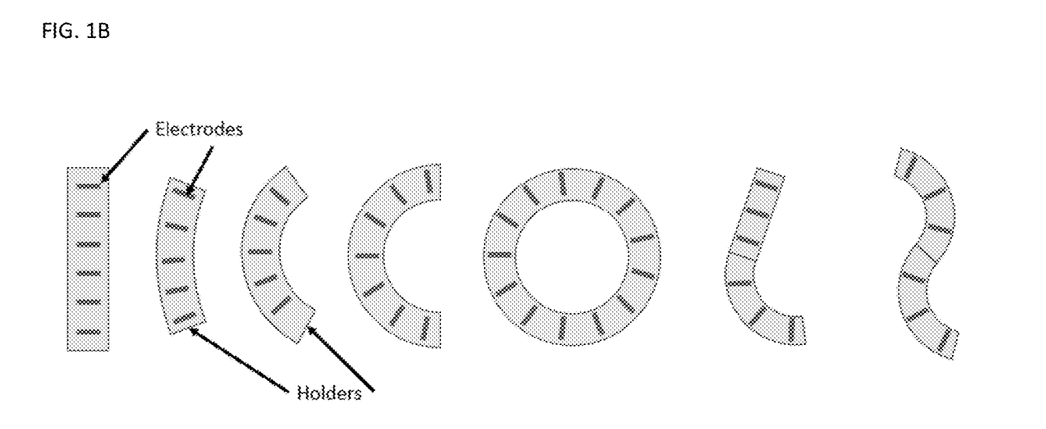
FIG. 1B provides a schematic depiction of various blade arrays that may be utilized in an ablation tool of the present invention.

The holder 5 may be any size or dimension suitable for application to a target organ or region of a target organ. Furthermore, the electrodes may be provided in a variety of configurations. For example, the holder 5 may be from 2 cm to 20 cm along the axis defined by the electrodes. In some preferred embodiments, the holder can include from 3 to 40, more preferably from 3 to 20 and most preferably from 3 to 10 electrodes. In some preferred embodiments, the electrodes are uniformly spaced. In preferred embodiments, the electrodes may be provided in a linear, curved, curvilinear, or circular arrangements or arrays. For example, FIG. 1A depicts a linear array of electrodes. In other embodiments, the electrodes may be arranged within the holder to provide an arrangement comprising one or more curves. Embodiments with curved arrays of electrodes can be circular or non-circular (i.e., the radius of curvature within an array can vary along the array). The curved arrays can have no inflection point ("C"-shaped), a single inflection point ("S"-shaped), or multiple inflection points. Embodiments with curvilinear arrays can preferably comprise linear (i.e., straight) section interspersed with one or more curved sections ("J"-shaped). Furthermore, the curved arrays can be open ("C"-shaped) or closed ("O"-shaped). FIG. 1B provides a schematic depiction of various blade arrays that may be utilized in an ablation tool of the present invention.

Figure 1C:
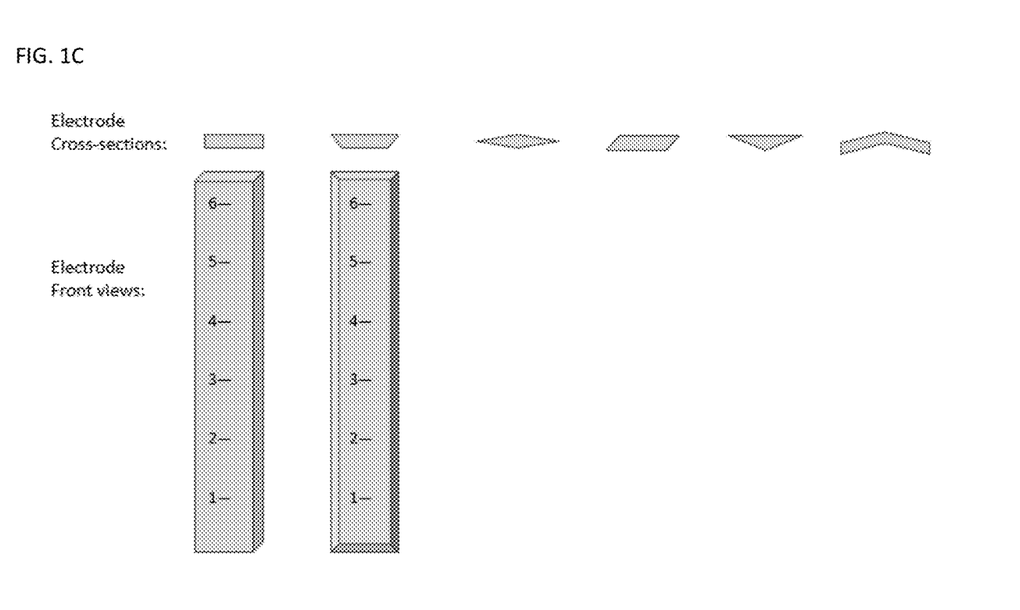
FIG. 1C provides a schematic depiction of various blade shapes that may be utilized in ablation tools of the present invention.

In preferred embodiments, the electrodes are blade-shaped. By "blade-shaped" it is meant that the electrodes have front and back planar portions and two side edge portions and the planar portions are wider that the edge portions to provide a blade shape. In some embodiments, the planar portions are flat such that the overall blade is flat and has a rectangular cross section. In other embodiments, the front and back surfaces may be curved, ridged, coined, concave, convex, etc. so that the blade does not have a rectangular cross section. In some embodiments, the blade-shaped electrodes can contain depth markings. FIG. 1C provides a schematic depiction of various blade shapes that may be utilized in ablation tools of the present invention.

Figure 1D:
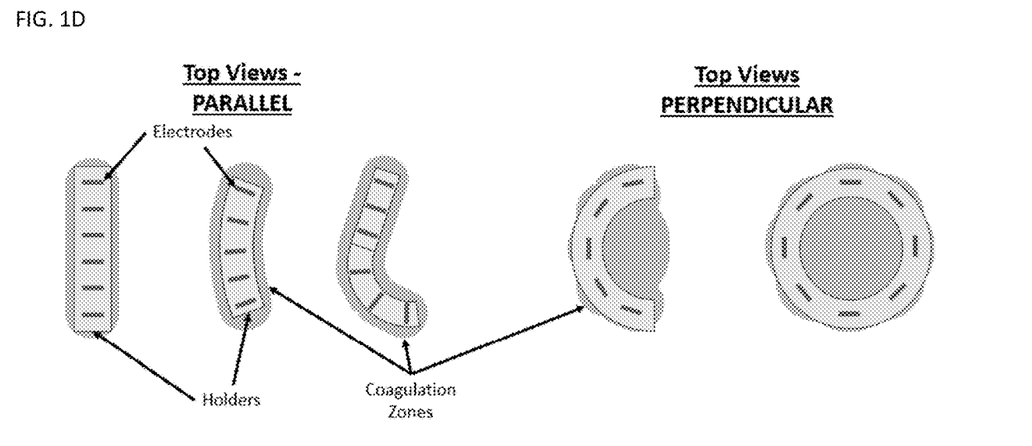
FIG. 1D provides a schematic depiction of embodiments of the invention where the orientation of the electrodes is varied to allow different uses of the systems.

Additionally, as depicted in the schematic diagram of FIG. 1D, in some embodiments the orientation of the electrodes can be varied to allow different uses of the systems. For example, if the electrodes are perpendicular to a radial line of a curved holder, the device can be used to coagulate a volume of tissue within the curvature of the array. Alternatively, if the electrodes are parallel to a radial line of the curved holder, the device is used to coagulate tissue between adjacent electrodes.

Holder 5 may be made of a material that is flexible or hinged in one or more planes in order to allow the user to dynamically change the geometry of the electrode array, for example, a linear array may be bent slightly in the plane of the large surface of the holder in order to avoid a critical anatomical structure that must remain intact. Additionally, holder 5 may be deformed/hinged out of plane in order to accommodate the shape of a structure, such as a roughly spherical tumor, which the user desires to treat. In some preferred embodiments, as described in more detail below, the electrodes 10 may be independently attached to an RF power source providing independently controllable RF power to each of the sets of elongate electrodes via cable 25.

The systems of the present invention are not limited to any particular RF ablation tool or electrode set. The ablation tool configurations depicted in FIGS. 1A-1D, while being preferred in some embodiments, are exemplary. In other embodiments, the individual electrodes depicted for the ablation tool in FIG. 1 may be substituted by electrode arrays comprising two or more needle-shaped electrodes as described in detail in application 62/811,136 which is incorporated herein by reference in its entirety (see also FIG. 8). In still other embodiments, the electrodes may be provided in a collapsible array as also described in application 62/811, 136.

One of the inherent challenges associated with energy application in the body is to constrain the energy to the region that the physician wants to treat in order to leave the surrounding tissues unaffected. Failure to achieve proper energy constraint has resulted in documented cases of life-threatening damage to surrounding organs.

In order to address these issues, the present invention provides a tissue separating backstop that can be used to electrically and/or thermally insulate a tissue or organ to which RF energy is being applied (e.g., a liver) during a surgical procedure (e.g., a resection) to insulate the organ from adjacent organs or tissues. In some preferred embodiments, the backstop is made from an electrically non-conductive material with low thermal conductivity. In some preferred embodiments, the backstop contains a plurality of tissue support structures that support the organ and provide separation from the upper surface of the backstop, significantly reducing thermal contact between the organ and the backstop and creating a thermal break. This reduces the RF thermal energy from heating surrounding tissues (including the surgeon's hand) via thermal conduction and results in faster coagulation of the tissues being treated. Speed is an important factor during liver surgery due to the highly vascular nature of the liver. During these surgeries, blood can be lost at a high rate, so rapid coagulation is essential to limit blood loss which is directly correlated with high rates of morbidity and mortality.

Figure 2:
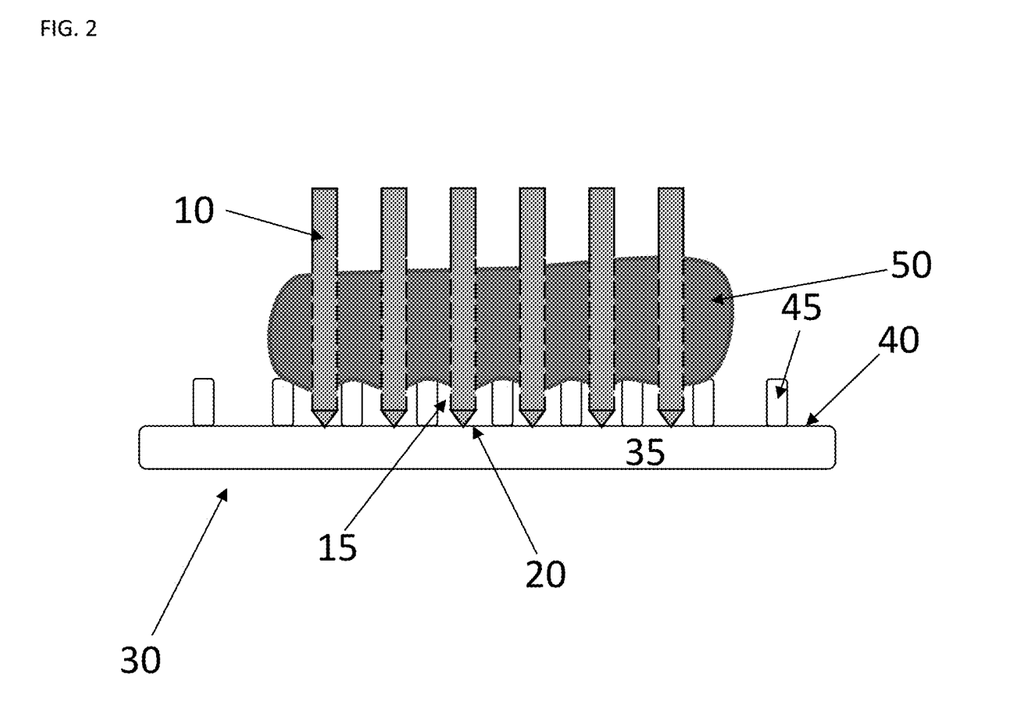
FIG. 2 is a cross-sectional view of a tissue separating backstop of the present invention with an organ positioned on the backstop and electrodes from an RF ablation tool extending through the organ.

Referring to FIG. 2, one embodiment of a tissue separating backstop 30 of the invention is depicted. The tissue separating backstop 30 preferably comprises a base portion 35 having an upper surface 40 from which a plurality of tissue support structures 45 project. In some preferred embodiments, the base portion 35 is sized to be held by the hand of a surgeon using the device. The tissue support structures 45 are preferably spaced so that when the tissue-separating backstop is brought into contact with organ 50, the organ 50 is supported on the tissue support structures and suspended above upper surface 40.

While the embodiments of the tissue separating backstop depicted in the Figures utilize a plate-shaped base portion, it will be understood that the base plate (and the backstop as a whole) may be provided in a variety of shapes and that the present invention is not limited to plate-shaped backstops. For example, the base portion can be curved in 1-dimension (e.g., a partial cylinder), or in 2-dimensions e.g., (a partial sphere), or in any desired shape. Thus, in addition to a planar or plate shape, the base portion may be curved, or for example, comprise rounded or curved portions to allow a comfortable grip of the backstop. As a further example, the base portion may comprise a curved projection suitable for grip by the hand of a surgeon.

Furthermore, the embodiments depicted in the Figures utilize pillar-shaped projections for support of the organ above the base portion. It will be understood that the tissue support structures may be varied in size and shape. For example, the tissue support structures may be pillars, ridges, rounded-cones, triangular cones, truncated cones, cylinders, and combinations thereof. In some preferred embodiments, the pillars may have a cross-section shape selected from the group consisting of circular, oval, elliptical, square and triangular cross-sections.

A benefit of the tissue separating backstop is that it enables uniform application of RF energy through the tissue being treated by allowing the distal portions 15 and sharpened tips 20 of the electrodes 10 to pass completely through the organ 50. The portion of the electrodes remaining in the tissue are uniform in thickness and not tapered which contributes to uniform electric fields and therefore uniform current which is responsible for heating the tissue. It is contemplated that the choice of tissue support structures allows electrode arrays of various geometries to pass adjacent to the tissue support structures to allow protrusion of the distal portions of the electrodes beyond the surface of the organ being treated.

Figure 3:
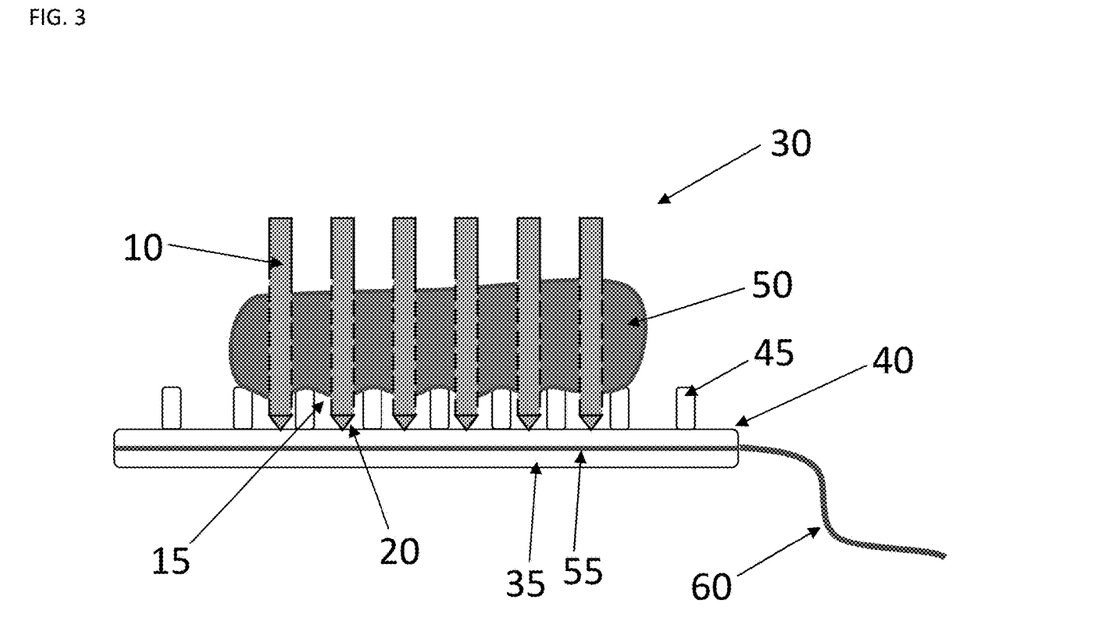
FIG. 3 is a cross-sectional view of a tissue separating backstop of the present invention with a conductive layer and further shown with an organ positioned on the backstop and electrodes from an RF ablation tool extending through the organ.

As mentioned above, the tissue separating backstop is preferably constructed from an insulating material, for example, a biocompatible plastic. In some embodiments, as depicted in FIG. 3, the tissue separating backstop 30 further contains a conductive layer 55 which can optionally be electrically connected to ground wire 60. This configuration preferable provides high frequency electrical shielding.

Figure 4:
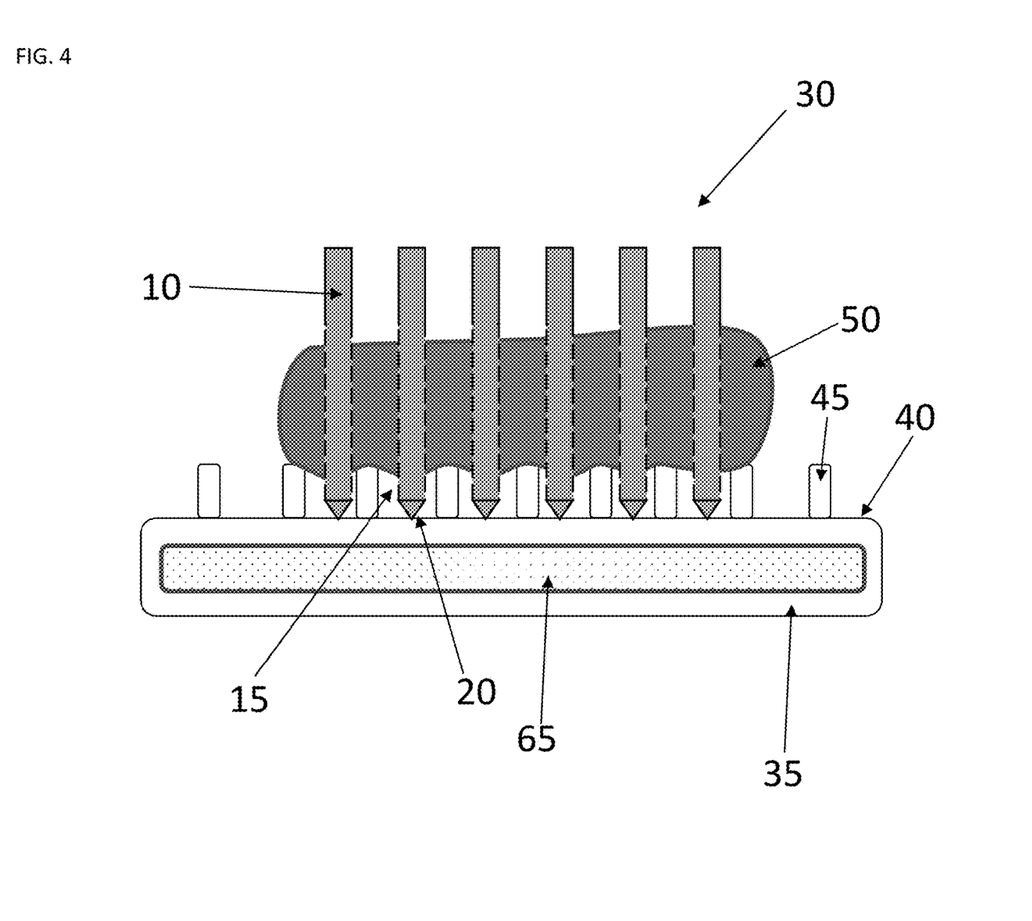
FIG. 4 is a cross-sectional view of a tissue separating backstop of the present invention with a hollow cavity to provide thermal insulation and further shown with an organ positioned on the backstop and electrodes from an RF ablation tool extending through the organ.

In still further embodiments as depicted in FIG. 4, a tissue separating backstop 30 of the present invention may comprise a cavity 65 in the base portion 35. It is contemplated that the cavity may provide additional insulation against transmission of thermal energy. In some embodiments, the cavity 65 may be filled with an insulating gas.

Figure 5:
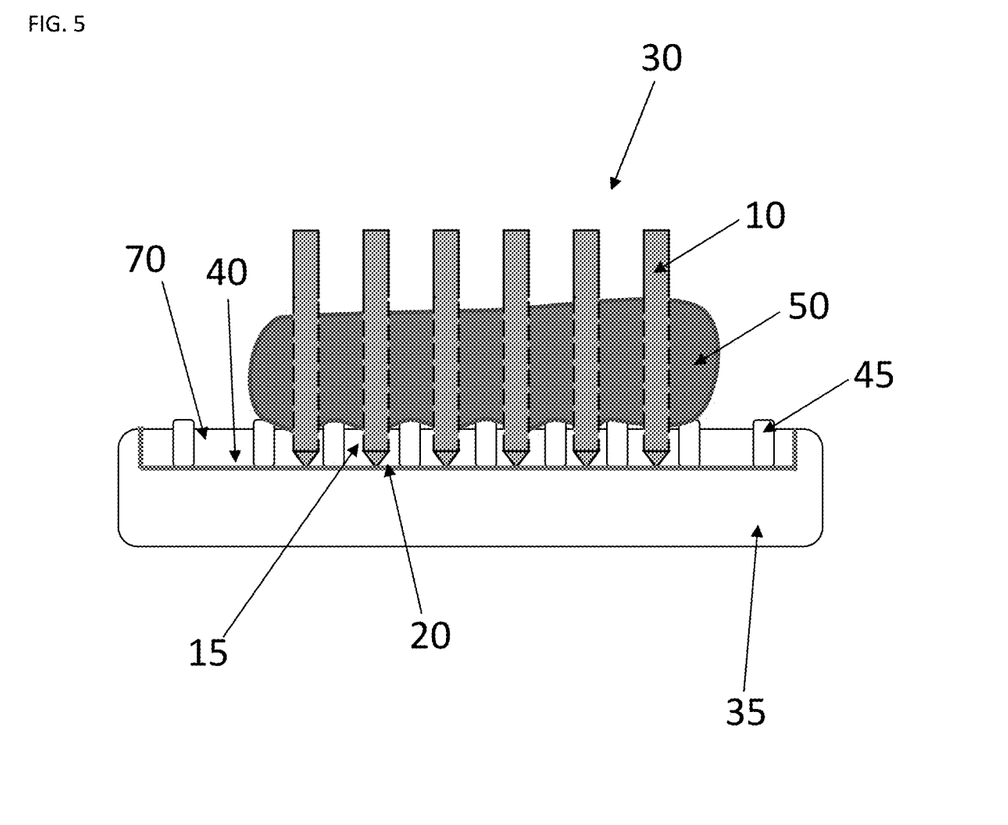
FIG. 5 is a cross-sectional view of a tissue separating backstop of the present invention where the tissue support structures are positioned in a fluid collecting tray feature.

In still other embodiments as depicted in FIG. 5, the base portion 35 of the tissue separating backstop 30 may comprise an indented tray portion 70. In some embodiments, the tissue support structures 45 are located in the tray portion 70. It is contemplated that the tray portion can collect hot liquid that may accumulate during an RF ablation procedure.

Figure 6:
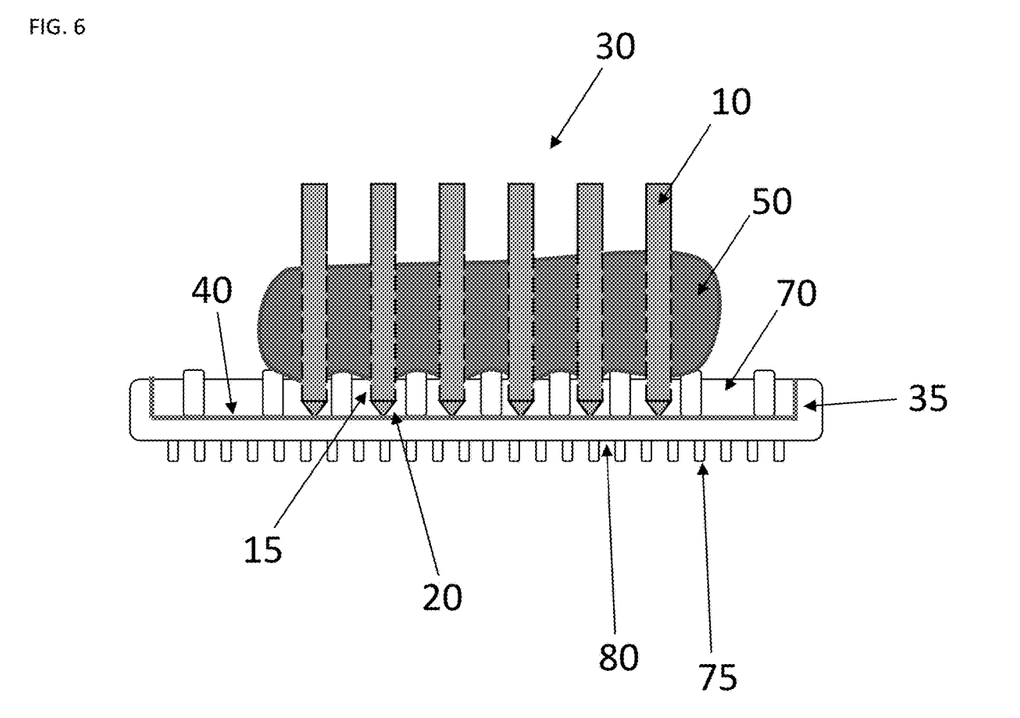
FIG. 6 is a cross-sectional view of a tissue separating backstop of the present invention with additional hand support structures on the lower side and further shown with an organ positioned on the backstop and electrodes from an RF ablation tool extending through the organ.

In other preferred embodiments as depicted in FIG. 6, a tissue separating backstop 30 of the present invention may further comprise a plurality of hand support structures 75 extending downward from the lower surface 80 of the base portion 35. It is contemplated that these hand support structures function to further minimize heat transfer from the organ 50 being treated to either the surgeon's hand or adjacent tissues. The embodiment depicted FIG. 6 utilize pillar-shaped projections as an example of hand support structures. It will be understood that the hand support structures may be varied in size and shape. For example, the hand support structures may be pillars, ridges, rounded-cones, triangular cones, truncated cones, cylinders, and combinations thereof. In some preferred embodiments, the pillars may have a cross-section shape selected from the group consisting of circular, oval, elliptical, square and triangular cross-sections.

The various features of the different embodiments of the tissue separating backstop described above can be used separately or in combination.

Figure 7:
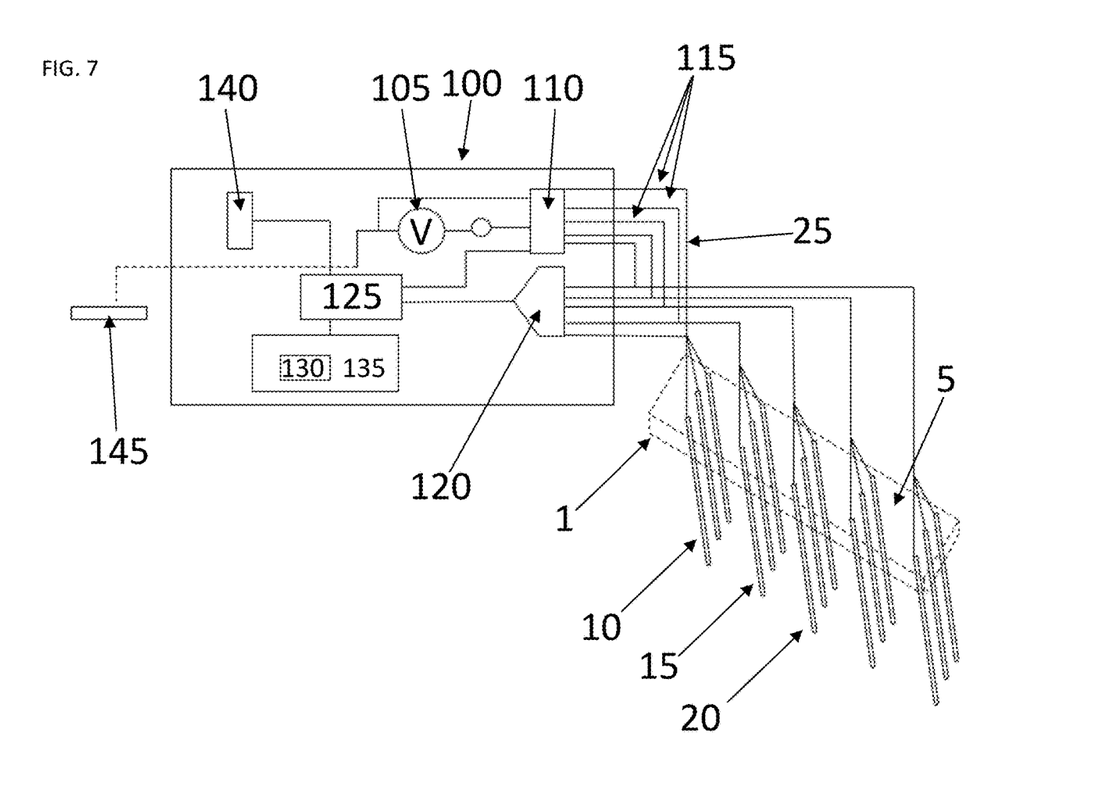
FIG. 7 is a block diagram of an RF power supply suitable for use with electrode arrays of the present invention.

In preferred embodiments, the tissue separating backstops are used in conjunction with an RF ablation system. The RF ablation system may be monopolar, bipolar or multipolar and may utilize devices comprising 1, 2, 3, 4, 5, 6, 7, 8, 9, 10 or more electrodes. FIG. 7 depicts an embodiment from a multipolar device. Referring to FIG. 7, an ablation tool 1 may be used in conjunction with a power unit 100 providing an RF power source 105. The power unit 100 provides power to elongate electrodes 10 (depicted as an array of electrode sets) via an electronically controllable switching circuit 110 communicating with the multiple conductors 115 of cable 25 (or cables) passing to the elongate electrodes 10. RF power sources 105 suitable for multiple electrodes are described in U.S. application Ser. No. 10/796,239 filed Mar. 9, 2004 and entitled Multipolar Electrode System for Volumetric Radio Frequency Ablation and U.S. application Ser. No. 10/167,681 filed Jun. 10, 2002 and entitled: Radio-Frequency Ablation System Using Multiple Electrodes, both hereby incorporated by reference in their entirety.

The power unit 100 may also receive signals from each of the elongate electrode 10 sets from optional thermal sensors (not shown), such as a thermocouple or solid-state temperature sensor, attached to the surface of the elongate electrodes or within the electrodes. Signals from these thermal sensors may be received by the power unit at input circuit 120 which digitizes and samples the temperature signals and provides them to a microprocessor 125. In a similar fashion, the power unit may receive voltage and current measurements from each electrode set and provide feedback based on calculated tissue impedance. In still other embodiments, the amount of power provided to electrode sets is monitored.

The microprocessor 85 executes a stored program 130 held in a memory 135 and also communicates with a front panel control set 140 to provide data to a user and accept user input commands.

While the present invention contemplates that power will be applied to the sets of elongate electrodes 10 in a bipolar mode as will be described, power unit 100 may alternatively communicate with a ground pad 145 to allow monopolar operation.

The switching circuit 110 provides switches that allow each conductor 115 attached to a set of elongate electrodes 10 to be switched to either terminal of the RF power source 65 so that the set of elongate electrodes 10 provides either a return or source of RF power. Switching circuit 110 may also be used to disconnect particular ones of the conductors 115 so as to isolate the associated set of elongate electrodes 10 and to allow a duty cycle modulated control of the power going to each set of elongate electrodes 10. Thus, while the power source 105 may optionally run at a constant rate, control of the power may be obtained through the switching circuit 110. It is desirable that switching of RF circuits occur only at the time that the voltage crosses zero volts. This is commonly known as "zero-crossing". In preferred embodiments, the switching circuit 110 is connected to the microprocessor 125 to be controlled thereby. For bipolar operation, each RF channel has two conductors. The voltage on a single RF conductor oscillates from −V to +V repeatedly. The two conductors from a single RF channel are out of phase so that when one is at +V, the other is at −V. The switching circuit can be used to supply RF power to multiple pairs of electrodes in sequence from a single channel RF generator, and it can be used to connect and disconnect the RF power to electrode pairs.

The microprocessor 125 in a preferred embodiment executes the program 130 in memory 135 to sequentially control the switches of the switching circuit 110 to connect one pair of sets of elongate electrodes 10 to the power source 110 at each time. Accordingly, at a time period 1, a pair of sets of elongate electrodes will be connected across power source 105 for current to flow therebetween. At this time, all other sets of elongate electrodes 10 are disconnected from the power source 105. At a second time period 2, a second pair of sets of elongate electrodes 15 will be connected across the power source 105 for power to flow therebetween and a previously utilized set of elongate electrodes is disconnected from the power source 105. In other embodiments, the power units incorporate a separate RF power source for each pair of electrodes so that all volumes of tissue may be energized at the same time. In still other preferred embodiments, multiple RF power sources are provided in the power unit and are used to energize pairs of electrodes sequentially.

This process repeats itself for the remaining sets of elongate electrodes 10 until each electrode has been pairwise connected to the power source 105. After this, the cycle is reinitiated.

In an alternative embodiment, each of the sets of elongate electrodes 10 other than the pair being connected to the power source 105 is connected to a return path so as to provide an effective virtual ground plane for return of current. In monopolar operation, only one set of electrodes is connected to the RF power source (as opposed to pairs) and the other connection of the RF power source is to a ground.

In yet another alternative embodiment, the sequential switching of pairs of sets elongate electrodes 10 does not proceed continuously from left to right but rather every other sequential pairing is skipped to allow cooling of the tissue near each energized electrode before the next adjacent pair is energized. Accordingly, a first pair of a set of elongate electrodes may be connected across the power source 105 and then a separate second pair, and then a separate third pair, and so forth.

As well as limiting the overheating of tissue, the switching of the sets of elongate electrodes 10 provides other benefits. A large number of sets of elongate electrodes 10 may create a very low impedance device which may be beyond the current capability of standard power sources 105. Accordingly, the switched operation also allows that power to be allocated among pairs of the sets of elongate electrodes 10. With standard power sources 105, the ablation region will typically be 1 to 2 cm wide and can be obtained in five to ten minutes. The switching among sets of elongate electrodes 10 may also eliminate shielding effects among electrodes providing a more uniform ablation region.

The amount of power deposited at the tissue surrounding each set of elongate electrodes 10 may be changed by varying the length of the duration for which the sets of elongated electrodes are energized. Alternatively, a high-frequency duty cycle modulation may be imposed on the power applied across the sets of elongated electrodes according to well-known techniques.

The control of power deposited at the tissue near each set of elongated electrodes 10 may be controlled by these techniques according to the temperature measured at each set of elongate electrodes 10, for example, to reduce power when the temperature rises above a pre-determined threshold either according to a simple thresholding technique or a more complex feedback loop using proportional, integral, and derivative terms.

As an alternative to temperature control, the impedance of the tissue between each pair of a set of elongated electrodes 10 may be determined by monitoring the current flow into the tissue and the particular voltage of the power source 105 (using an in-line current sensor), and this impedance can be used to control power by decreasing, or shutting down power for a certain time period as impedance rises, the latter indicating a heating of the tissue.

Impedance measurements can also be used to gauge the thickness of the tissue being ablated. The tissue may have different thickness in the slice where the electrode array assembly 1 is inserted. By measuring impedance (with low power application of RF current) between adjacent sets of elongated electrodes 10, the slice thickness along the electrodes 10 can be estimated before ablating the slice. Power applied between each electrode pair can then be applied according to tissue thickness (e.g. tissue twice as thick requires approximately twice the power). In one embodiment, this can be achieved by applying a constant voltage bipolar between each electrode pair. If tissue is twice as thick, impedance is about half as great, and as a result the applied power is twice as high with that constant voltage.

Monitoring current and voltage with the microprocessor 125 may also be used to detect excess or low currents to any particular set of elongate electrodes 10. In the former case, power limiting may be imposed. The latter case may indicate a disconnection of one or more sets of elongate electrodes 10 and an indication of this may be provided on the front panel control set 140 to the user.

It will be apparent to those of ordinary skill in the art that a number of other control feedback techniques may be used including those which control current flow or voltage or power (the latter being the product of current and voltage) according to each of these terms.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A system for use in coagulation of a resection line in a human liver comprising:
   a radio frequency (RF) power source;
   a series of three or more blade-shaped electrodes that are electrically connected to the RF power source, the three or more blade-shaped electrodes having a length so that the electrodes extend through the liver during coagulation of the resection line, the three or more blade-shaped electrodes further each having a tissue-piercing distal end and wherein the three or more blade-shaped electrodes in the series each comprise two opposing parallel planar surfaces that extend along the length of the blade-shaped electrodes defining a width and a planar axis and two opposing edges defining a thickness and each of the three or more blade-shaped electrodes are characterized in having a greater width than thickness;
   an electrically insulated holder, the three or more blade shaped electrodes non-slidably positioned in the electrically insulated holder, wherein the three or more blade-shaped electrodes are oriented so that when alternating current power is applied via the RF power source to a pair of blade-shaped electrodes within the series of three or more blade-shaped electrodes in the electrically insulated holder a current flows between the pair of blade-shaped electrodes; and
   a backstop formed from an electrically non-conductive material,
      the backstop having an upper surface and a lower surface and a plurality of tissue support structures extending upward from the upper surface of the backstop,
      the tissue support structures spaced to support the liver above the upper surface of the backstop when the backstop is placed underneath the organ and sized to receive the tissue piercing distal ends of the three or more blade-shaped electrodes positioned in the electrically insulated holder so that the tissue piercing distal portions of the three or more blade-shaped electrodes pass through and extend beyond the liver and the tissue piercing distal portions contact the upper surface of the backstop,
   wherein the backstop and the electrically insulated holder are independently positionable.

2. The system of claim 1, wherein the series of three or more blade shaped electrodes comprises from three to ten blade-shaped electrodes.

3. The system of claim 1, wherein the series of three or more blade-shaped electrodes are positioned in the electrically insulated holder in an array selected from the group consisting of a linear array, a curved array, a curvilinear array, a circular array, an oval array and an elliptical array.

4. The system of claim 1, wherein the electrically insulated holder is curved to define a series of radial lines from the center of the curve and the series of three or more blade-shaped electrodes are positioned in the curved electrically insulated holder so that the planar axes of the blade-shaped electrodes are parallel to the radial lines of the curved electrically insulated holder.

5. The system of claim 1, wherein the electrically insulated holder is curved to define a series of radial lines from the center of the curve and the series of three or more blade-shaped electrodes are positioned in the electrically insulated holder so that the planar axes of the blade-shaped electrodes are perpendicular to the radial lines of the curved electrically insulated holder.

6. The system of claim 1, wherein the electrically insulated holder is a linear electrically insulated holder having a long axis, wherein the three or more blade shaped electrodes are positioned in the electrically insulated holder so that the planar axes of the blade-shaped electrodes are perpendicular to the long axis of the linear electrically insulated holder.

7. The system of claim 1, wherein the three or more blade-shaped electrodes in the series are uniformly spaced in the electrically insulated holder.

8. The system of claim 1, wherein the RF power source comprises a multi-channel RF generator with dedicated RF amplifiers for selected adjacent pairs of the three or more blade-shaped electrodes.

9. The system of claim 8, wherein the RF power source applies the alternating current to adjacent pairs of blade-shaped electrodes within the series of three or more blade-shaped electrodes.

10. The system of claim 8, wherein the RF power source applies the alternating current to non-adjacent pairs of blade-shaped electrodes within the series of three or more blade-shaped electrodes.

11. The system of claim 1, wherein the backstop has a shape selected from the group consisting of a planar shape, and rounded shape, a curved shape, a partial cylindrical shape and a partial spherical shape.

12. The system of claim 1, wherein the tissue support structures have a shape selected from the group consisting of pillars, ridges, rounded-cones, triangular cones, truncated cones, cylinders, and combinations thereof.

13. The system of claim 1, wherein the backstop further contains a conductive layer between the upper and lower surfaces.

14. The system of claim 13, wherein the conductive layer is attached to a ground.

15. The system of claim 1, wherein the backstop has a thermal break positioned between the upper and lower surfaces.

16. The system of claim 1, wherein the electrically insulated holder comprises a thermal break provided by a hollow cavity positioned between the upper and lower surfaces of the electrically insulated holder.

17. The system of claim 1, wherein the backstop further has a rim extending around the perimeter of the backstop to provide a basin for receiving fluid expressed from the organ during ablation.

18. The system of claim 1, wherein the lower surface of the backstop comprises a plurality of hand support structures extending therefrom to reduce heat transfer from the backstop to the hand of a user.

19. The system of claim 18, wherein the hand support structures are selected from the group consisting of pillars, ridges, rounded-cones, triangular cones, truncated cones, cylinders, and combinations thereof.

* * * * *